United States Patent
Al-Mayouf et al.

(10) Patent No.: US 10,488,323 B1
(45) Date of Patent: Nov. 26, 2019

(54) STEEL PANEL WITH AN INTEGRATED CORROSION SENSOR

(71) Applicant: KING SAUD UNIVERSITY, Riyadh (SA)

(72) Inventors: Abdullah Mohammed Al-Mayouf, Riyadh (SA); Matar Naif Al-Shalwi, Riyadh (SA)

(73) Assignee: King Saud University, Riyadh (SA)

(*) Notice: Subject to any disclaimer, the term of this patent is extended or adjusted under 35 U.S.C. 154(b) by 0 days.

(21) Appl. No.: 16/355,687

(22) Filed: Mar. 15, 2019

(51) Int. Cl.
| | |
|---|---|
| *G01N 17/02* | (2006.01) |
| *G01N 17/00* | (2006.01) |
| *G01N 17/04* | (2006.01) |
| *G08B 21/18* | (2006.01) |
| *G01R 19/25* | (2006.01) |

(52) U.S. Cl.
CPC ........... *G01N 17/006* (2013.01); *G01N 17/02* (2013.01); *G01N 17/04* (2013.01); *G01R 19/25* (2013.01); *G08B 21/18* (2013.01)

(58) Field of Classification Search
CPC . G01N 27/02; G01N 27/04–046; G01N 17/02
See application file for complete search history.

(56) References Cited

U.S. PATENT DOCUMENTS

| | | | | |
|---|---|---|---|---|
| 3,680,531 A | * | 8/1972 | Holdt | F22B 37/42 122/379 |
| 5,712,612 A | | 1/1998 | Lee et al. | |
| 7,239,156 B1 | * | 7/2007 | Hladky | G01N 17/02 204/404 |

(Continued)

FOREIGN PATENT DOCUMENTS

| | | | | |
|---|---|---|---|---|
| DE | 102012107792 | * | 1/2014 | ............ G01N 17/04 |
| JP | 2011220717 A | * | 11/2011 | ............ G01N 27/26 |

(Continued)

OTHER PUBLICATIONS

EPO computer-generated English language translation of Isomoto Y. JP 2011220717, patent published Nov. 4, 2011, downloaded May 14, 2019. (Year: 2019).*

(Continued)

*Primary Examiner* — Alexander S Noguerola
(74) *Attorney, Agent, or Firm* — Richard C. Litman; Nath, Goldberg & Meyer (57) ABSTRACT

The steel panel with an integrated corrosion sensor is a steel panel having an integrated sensor for monitoring dissolution of a magnetite layer during acid cleaning of the steel panel. The steel panel has an opening formed therethrough, and a hollow insulator is secured to the steel panel within the opening. The hollow insulator is formed from an electrical insulation material and electrically isolates the steel panel from a steel core, which is mounted within the hollow insulator. A reference electrode is positioned near the steel panel. A voltmeter is electrically connected between the reference electrode and a first surface of the steel core. An opposed second surface of the steel core has a layer of magnetite formed thereon. An alarm is in electrical communication with the voltmeter, such that the alarm generates an alarm signal when the voltmeter detects a corrosion potential at a preset threshold potential.

7 Claims, 7 Drawing Sheets

(56) References Cited

U.S. PATENT DOCUMENTS

2010/0280665 A1* 11/2010 Fildes .................. F24H 9/2035
700/275
2016/0091413 A1   3/2016 Kim et al.

FOREIGN PATENT DOCUMENTS

KR   101071863 B1   10/2011
RU     2085906 C1    7/1997

OTHER PUBLICATIONS

EPO computer-generated English language translation of Bernd Epple DE 2012 107792 B3, patent published Jan. 16, 2014, downloaded May 14, 2019. (Year: 2019).*
Covino Jr. et al. Electrochemical corrosion rate probes for high temperature energy applications. No. DOE/ARC-2004-023. Albany Research Center (ARC), Albany, OR, 2004.

* cited by examiner

STEEL PANEL WITH AN INTEGRATED CORROSION SENSOR

BACKGROUND

1. Field

The disclosure of the present patent application relates to the acid cleaning of steel walls and panels, such as those found in steam boilers, and particularly to a steel panel with an integrated corrosion sensor for monitoring dissolution of a magnetite layer on the steel panel during acid cleaning of the panel.

2. Description of the Related Art

Steam boilers, such as those typically found in power plants and the like, are commonly made from carbon steel. The surface of the water side of the boiler develops undesirable deposits during use which must then be removed. Such deposits typically have a lower thermal conductivity than steel, thus making it necessary to raise the temperature on the combustion side of the boiler. This results in lower efficiency for the boiler, making it necessary to use more fuel to generate steam. Since the heat transfer efficiency of the boiler reduces as a function of the deposit build-up, frequent cleaning of the water side of the boiler must be performed.

At a specific elevated temperature, steam reacts with the iron ions on the boiler wall steel (on the water side), forming a relatively uniform layer of magnetite ($Fe_3O_4$). In a reducing atmosphere at temperatures above 100° C., the water acts as an oxidizing agent, causing an electrochemical reaction to take place, resulting in the magnetite layer. The magnetite layer is a typically black, extremely thin adherent film that passivates the steel surface and therefore protects it from corrosion. The layer of magnetite is thus a desirable deposit in a steam boiler and, in an ideal situation, the water side of a boiler would be coated with just this thin film of magnetite. This is often achieved by using a boiler water treatment program. However, in time, the magnetite ages, resulting in a layer that is porous and can eventually become detached from the steel surface.

When the magnetite layer has degraded, as described above, there is an increased chance of excessively thick localized deposits, resulting in a magnetite film which is no longer thin or strong. In addition to the negative effect on heat transfer, such irregularities also form a source of adhesion for other undesirable salt deposits, such as calcium carbonate. When the efficiency of the steam boiler becomes too low or when there is a possibility of blockages and leaks, the decision is then typically made to clean the water side of the boiler chemically.

The chemical cleaning of the steel walls of the boiler is typically performed by first degreasing the water side surface, followed by pickling with a hydrochloric acid or a mixture of hydrofluoric acid and hydrochloric acid. The pickling is followed by passivating with ammonium citrate and an oxidizing agent. During the pickling phase, which is carried out by circulating a warm inhibiting acid, the magnetite reacts with the acid. During this process, the iron concentration in the cleaning fluid will increase. Because the requirement is to dissolve the deposit and protect the bare steel against the corrosive action of acids, an inhibitor is then typically added to the acidic solution. The inhibitor will reduce the corrosion rate to a value less than 50 mpy. The iron content in the cleaning fluid is therefore a parameter that must be continuously determined in order to give a clear indication of how the cleaning is proceeding. When the iron content stabilizes, the magnetite is determined to have been fully dissolved, drawing the pickling phase to a close.

The traditional cleaning process described above requires continuous monitoring of the iron content in the cleaning fluid, which is a time-consuming and laborious procedure. The necessity of coupling this monitoring with the addition of the inhibitor adds great expense to the process and, further, introduces environmental concerns into the cleaning process. It would obviously be desirable to be able to more directly determine the point at which the magnetite has dissolved, but before acid corrosion of the steel can occur. Thus, a steel panel with an integrated corrosion sensor solving the aforementioned problems is desired.

SUMMARY

The steel panel with an integrated corrosion sensor is a steel panel, such as those used in the construction of steel boilers and the like, having an integrated sensor for monitoring dissolution of a magnetite layer on the panel during acid cleaning of the steel panel. The steel panel has an opening formed therethrough, and a hollow insulator is secured to the steel panel within the opening. The hollow insulator is formed from an electrical insulation material, such as an epoxy resin, and electrically isolates the steel panel from a steel core, which is mounted within the hollow insulator.

A reference electrode, such as a saturated calomel electrode (SCE), is positioned near the steel panel. In a steam boiler, for example, the reference electrode would be positioned inside the steam boiler near the water side of the steel panel forming the steam boiler's wall. A voltmeter is electrically connected between the reference electrode and a first surface of the steel core. In the example of a steam boiler, the first surface of the steel core would be positioned outside the steam boiler. An opposed second surface of the steel core would be positioned inside the steam boiler, where a layer of magnetite would form thereon through electrochemical reaction with the steam. An alarm is in electrical communication with the voltmeter, such that the alarm generates an alarm signal when the voltmeter detects a corrosion potential at a preset threshold potential.

In use, returning to the example of a steam boiler, hydrochloric acid or a mixture of hydrochloric acid and hydrofluoric acid may be used to dissolve the magnetite layer built up on the water side of the steel walls. Initially, the voltmeter measures a mixed potential between the reference electrode (in the acid cleaning solution within the steam boiler) and the combined steel core and magnetite layer formed thereon. As the magnetite layer formed on the second surface of the steel core dissolves, the measured mixed potential changes, tending towards the potential of just steel. The preset threshold potential is set to a potential just prior to the potential representative of pure steel, i.e., the point at which the steel itself would begin dissolving in the acid cleaning solution. At this point, an alarm signal is generated, indicating that the cleaning process should end.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
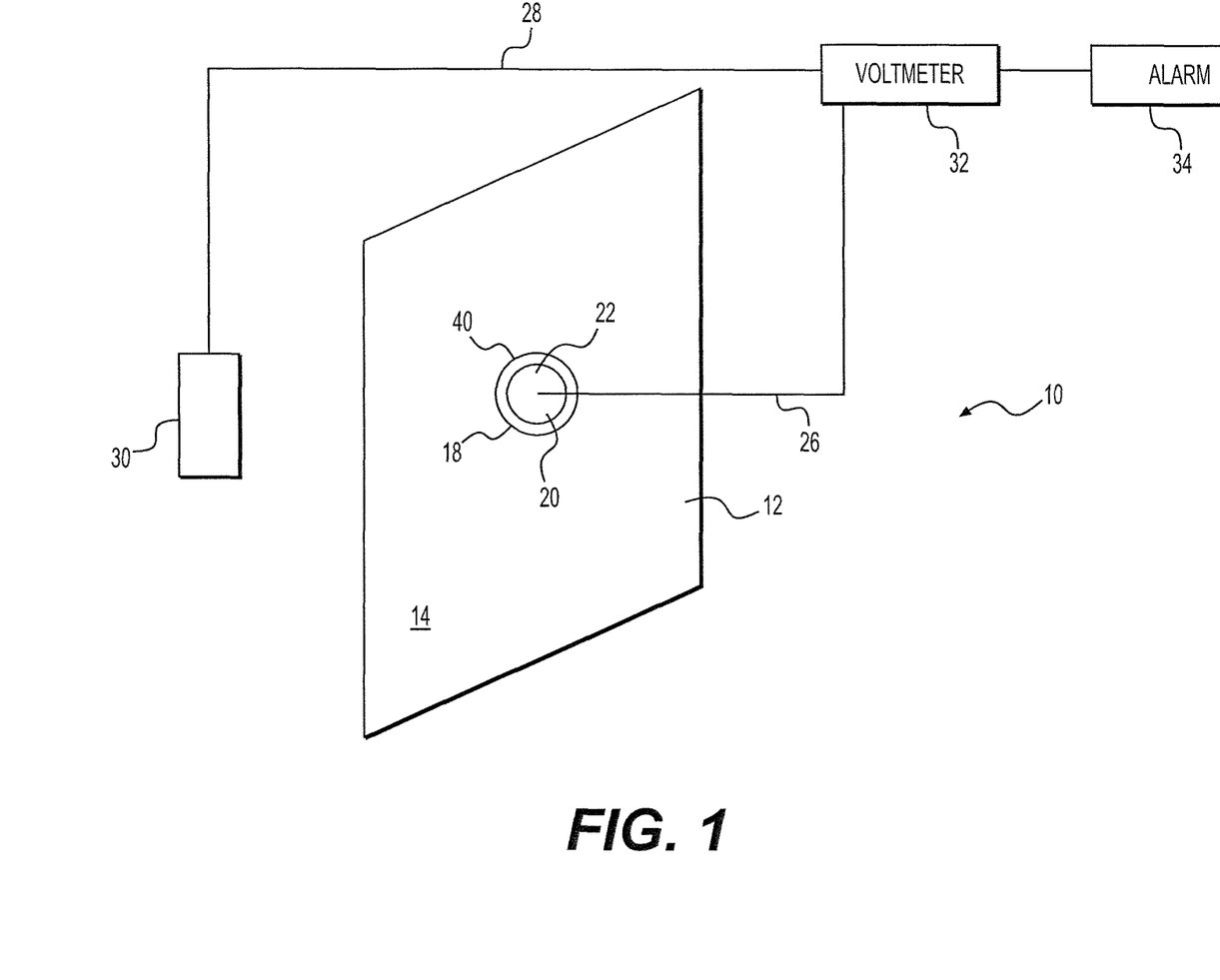
FIG. 1 is diagram of a steel panel with an integrated corrosion sensor.
Figure 2:
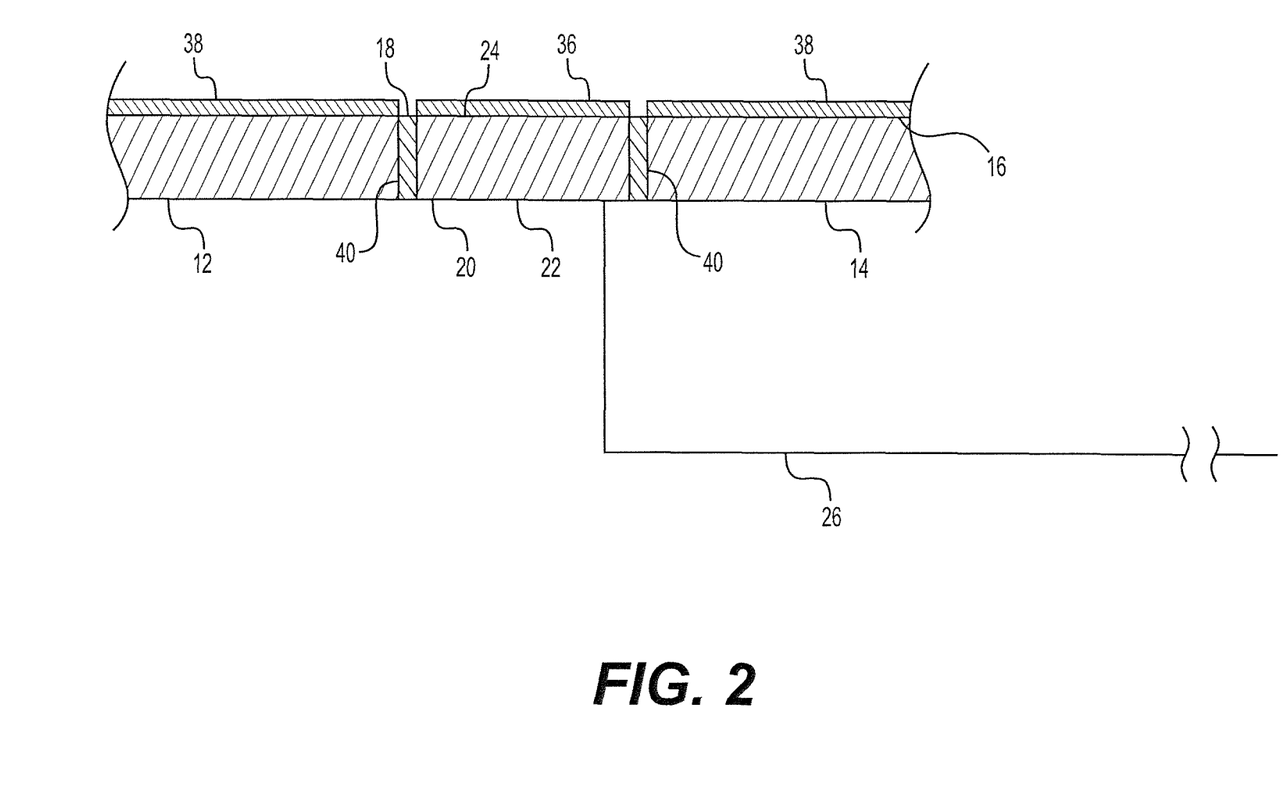
FIG. 2 is a partial side view in section of the steel panel of FIG. 1.

The steel panel with an integrated corrosion sensor 10 is a steel panel 12, such as those used in the construction of steel boilers and the like, having an integrated sensor for monitoring dissolution of a magnetite layer during acid cleaning of the steel panel. As shown in FIGS. 1 and 2, the steel panel 12 has an opening 40 formed therethrough, and a hollow insulator 18 is secured to the steel panel 12 within opening 40. The hollow insulator 18 is shown as a substantially cylindrical ring in FIG. 1. However, it should be understood that the hollow insulator 18 may have any suitable dimensions and configuration. It should be further understood that the hollow insulator 18 may be formed from any suitable type of electrical insulation material. For example, the hollow insulator 18 may be formed from an epoxy resin. The hollow insulator 18 electrically isolates the steel panel 12 from a steel core 20, which is mounted within the hollow insulator 18.

A reference electrode 30 is positioned near the steel panel 12. It should be understood that any suitable type of reference electrode may be used. For example, the reference electrode 30 may be a saturated calomel electrode (SCE). In a steam boiler, for example, the reference electrode 30 would be positioned inside the steam boiler near the water side of the steel panel 12 forming the steam boiler's wall. A voltmeter 32 is electrically connected between the reference electrode 30 and a first surface 22 of the steel core 20. In the example of a steam boiler, the first surface 22 of the steel core 20 would be positioned outside the steam boiler. An opposed second surface 24 of the steel core 20 would be positioned inside the steam boiler, where a layer of magnetite 36 would form thereon through electrochemical reaction with the steam.

In FIG. 2, the first surface 22 of the steel core 20 is shown substantially aligned with a first surface 14 of the steel panel 12, and the second surface 24 of the steel core 20 is shown substantially aligned with the second surface 16 of the steel panel 12. Although such alignment is not necessary, it should be understood that the steel panel 12 forms a wall, panel or other structural element of a larger steel structure, and as such, the hollow insulator 18 and the steel core 20 should form a structurally sound and continuous set of panel surfaces with the steel panel 12. In FIG. 2, an exemplary thin film of magnetite 38 is shown built up on the second surface 16 of the steel panel 12. In a steam boiler, as an example, the second surface 16 would be the water side of the steel wall forming the boiler, and the magnetite layer 38 would be the naturally occurring magnetite formed through electrochemical reaction between the steel and the steam. The thin film of magnetite 36 formed on the second surface 24 of the steel core 20 may be similarly naturally formed (i.e., formed during use of the steam boiler, for example), or may be artificially formed, such as through epitaxial growth, thin film deposition, sputtering or the like.

An alarm 34 is in electrical communication with the voltmeter 32, such that the alarm 34 generates an alarm signal when the voltmeter 32 detects a corrosion potential at a preset threshold potential. It should be understood that the alarm 34 may be an audio alarm, visual alarm, a combination thereof or any other suitable type of alarm for generating an alarm signal when the preset threshold potential has been reached. In FIGS. 1 and 2, the voltmeter 32 is shown connected to the first surface 22 of steel core 20 by a cable 26. It should be understood that the cable 26 may be any suitable type of wire or cable. Similarly, in FIG. 1, the voltmeter is shown connected to the reference electrode 30 by cable 28. It should be understood that the cable 28 may be any suitable type of wire or cable, and that the cable 28 may pass through the steel panel 12, if necessary, in any suitable way such that cable 28 is electrically insulated from the steel panel 12.

In use, returning to the example of a steam boiler, hydrochloric acid or a mixture of hydrochloric acid and hydrofluoric acid may be used to dissolve the magnetite layer built up on the water side of the steel walls, i.e., the magnetite layer 38 formed on the second surface 16 of the steel panel 12. Initially, the voltmeter 32 measures a mixed potential between the reference electrode 30 (in the acid cleaning solution within the steam boiler) and the combined steel core 20 (measured at the pure steel first surface 22) and magnetite layer 36. As the magnetite layer 36 formed on the second surface 24 of the steel core 20 dissolves, the measured mixed potential changes, tending towards the potential of just steel without a magnetite layer. The preset threshold potential is set to a potential just prior to the potential representative of pure steel, i.e., the point at which the steel itself would begin dissolving in the acid cleaning solution. At this point, an alarm signal is generated, indicating that the cleaning process should end before dissolving or corroding the steel.

In order to test the steel panel with an integrated corrosion sensor 10, magnetite powder was mixed with polyvinyl alcohol solution (as a binder) and formed into pellets through pressing at a pressure of 7 tons/cm². The pellets were sintered in the presence of nitrogen gas flow. The temperature was gradually increased by 50° C. increments and was held for 30 minutes at 900° C., and then decreased gradually. Steel samples were machined from a steel rod with the following composition: C (0.2%), Mn (0.94%), Si (0.31%) and Fe (98+%). A magnetite coating was formed on steel coupons in an autoclave containing 1M sodium hydroxide solution with excess hydrazine solution. The autoclave was heated in an oven with a gradual increase in temperature until reaching 180° C. for 24 hours.

Figure 3:
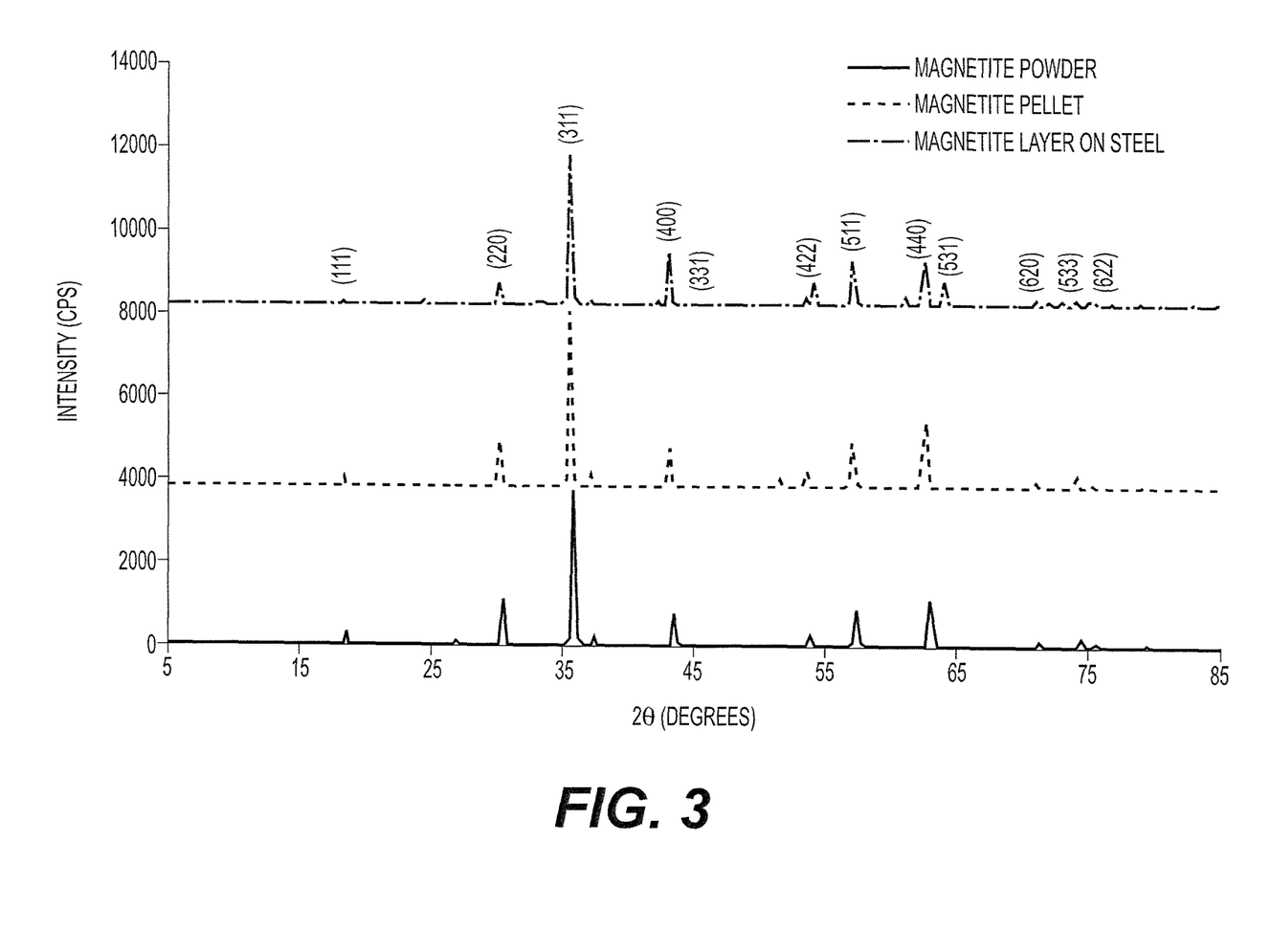
FIG. 3 is an X-ray diffractogram comparing X-ray diffraction (XRD) results for magnetite powder, a magnetite pellet, and a magnetite layer formed on a steel surface.

The combined steel and magnetite electrode was formed by attaching the magnetite pellet (prepared at varying thicknesses for purposes of testing) to a cylinder of steel having a matching diameter. The electrode and the steel cylinder were covered with an epoxy resin, while the magnetite was left exposed for eventual exposure to the cleaning solution. FIG. 3 shows the results of X-ray diffraction (XRD) performed on the magnetite powder, the magnetite pellet, and the magnetite layer attached to the steel surface. XRD was performed with a MiniFlex benchtop powder X-ray diffraction instrument manufactured by Rigaku® Corporation of Tokyo, Japan, with Cu Kα radiation at 40 kV and 15 mA. In order to make sure that the magnetite preserved its chemical nature after sintering, the XRD measurements, as shown in FIG. 3, were conducted on both the magnetite powder (before sintering), with the magnetite pellets and magnetite layer both grown on the steel surface. The XRD patterns for the magnetite powder and the magnetite pellet shown in FIG. 3 are identical for both samples, and are also consistent with the International Centre for Diffraction Data index for magnetite (ICDD 01-071-6338).

Figure 4:
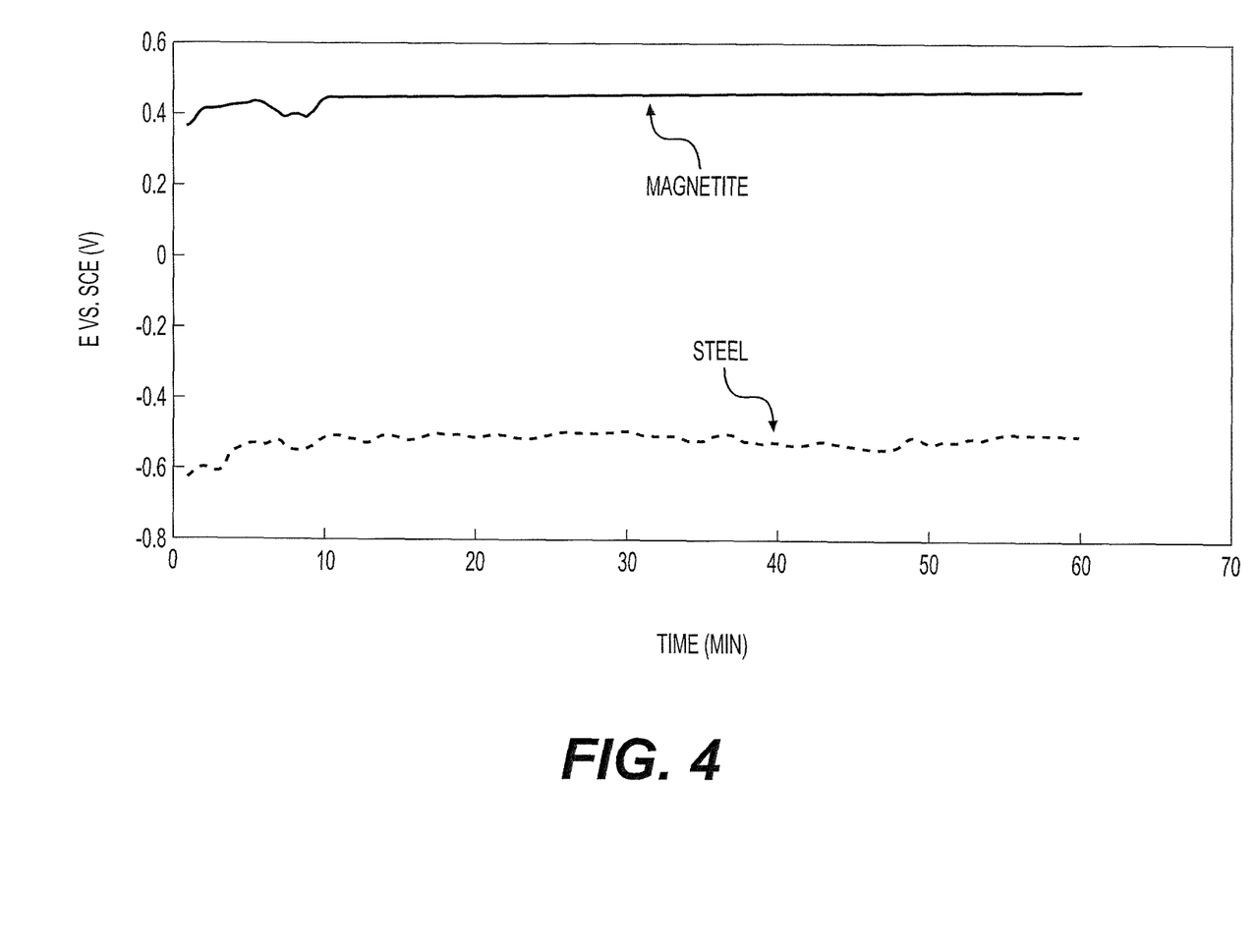
FIG. 4 is a graph comparing potential-time curves for a steel electrode and a magnetite electrode vs. a standard calomel electrode (SCE) in 5% HCl solution at 60° C.

Potential and linear polarization measurements were conducted in 5% hydrochloric acid (HCl) solution at 60° C. using a saturated calomel electrode (SCE) as a reference electrode and a platinum electrode as an auxiliary electrode. The solution was stirred using a magnetic stirrer. Potential measurements were also carried out for individual electrodes under the same conditions. FIG. 4 shows the variation of potential with time for the magnetite and steel in 5% HCl at 60° C. as single electrodes. The values shown are the average of three measurements with a standard deviation between 0.002 V and 0.08 V. The potential of the magnetite electrode is nearly constant and very different from that of the steel electrode. Magnetite dissolves according to the reaction:

$$Fe_3O_4 + 2e + 8H^+ \rightarrow 3Fe^{2+} + 4H_2O, \quad (1)$$

with a potential (E) given by the equation:

$$E_{Fe_3O_4/Fe^{2+}} = E^O - \frac{RT}{2F}\ln\frac{[Fe^{2+}]^3}{[H^+]^8}, \quad (2)$$

where E°=0.98 V vs. NHE. Steel corrodes according to the reaction:

$$Fe \rightarrow Fe^{2+} + 2e \quad (3)$$

and its free potential is given the equation:

$$E_{Fe/Fe^{2+}} = -0.440 + \frac{RT}{2F}\ln[Fe^{2+}]. \quad (4)$$

Reactions (1) and (3) represent the free dissolution of both magnetite and steel, respectively, without the contribution of the other reaction.

Figure 5:
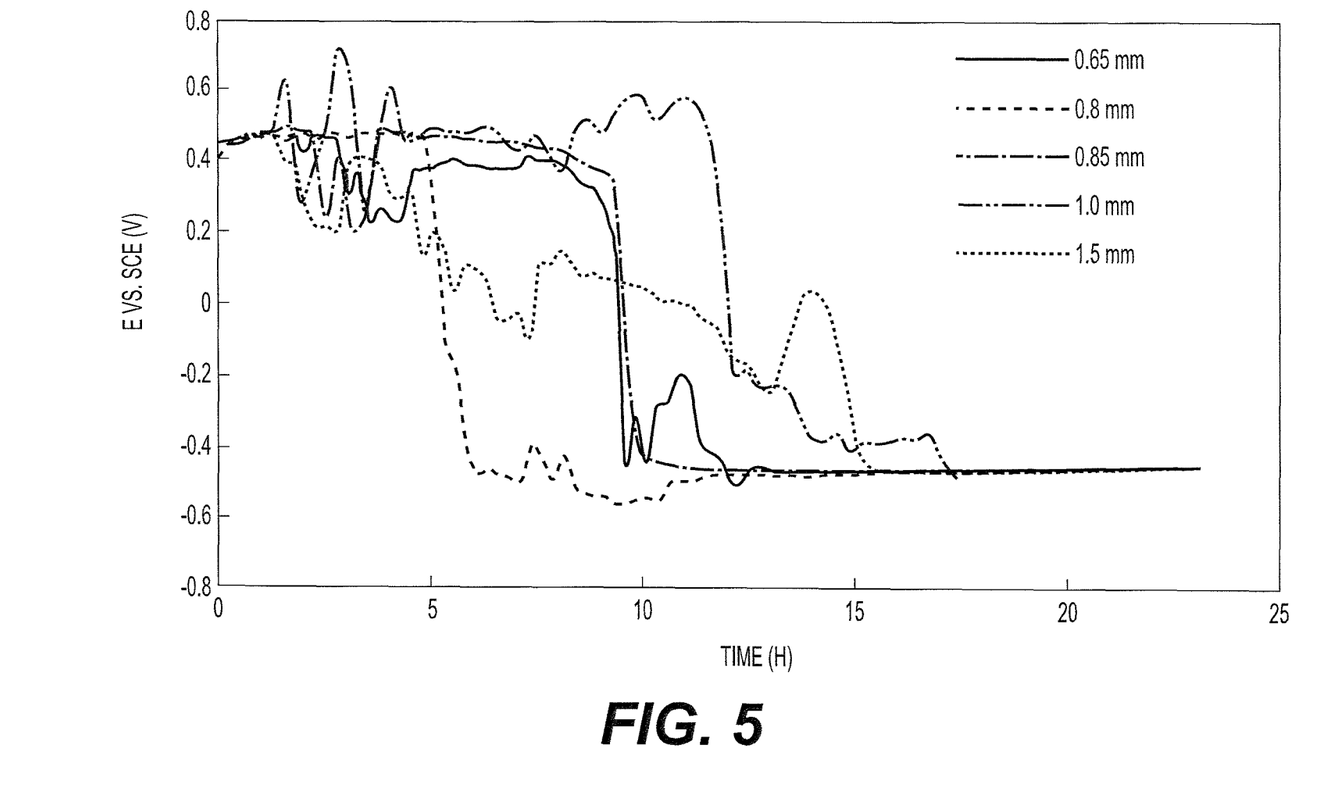
FIG. 5 is a graph comparing potential-time curves for magnetite layers formed on steel surfaces vs. a saturated calomel electrode (SCE) in 5% HCl solution at 60° C., where the magnetite layer samples being compared have thicknesses of 0.65 mm, 0.8 mm, 0.85 mm, 1.0 mm and 1.5 mm, respectively.

In another series of measurements, magnetite pellets with variable thickness were attached to steel electrodes, and the potential was measured as a function of time. FIG. 5 shows a typical potential-time curve in which the measured potential was similar to that of the magnetite electrode. After some time, which is dependent upon the thickness of the magnetite pellet, the potential started to change to more active values until it reached that of the steel electrode, as shown in FIG. 4. Similar potential-time variation was observed for carbon steel samples obtained from boilers with magnetite formed on the surface.

The observed potential during the first part of immersion indicates that magnetite is dissolving freely with no contribution from steel dissolution. As dissolution progresses, the magnetite thickness is reduced and/or becomes more porous, exposing a small area of steel. The steel then starts to contribute to the measured potential in a manner that depends on the exposed area of steel. The potential of the magnetite/iron couple is a mixed potential. The observed potential is controlled by the rates of all processes occurring at the same rate at that potential, which includes magnetite and iron dissolutions and hydrogen gas evolution.

The potential of a galvanic couple between magnetite and iron presents a potential that depends on area ratios between the magnetite and iron, which tends to be closer to that of iron as the area of the iron increases. The short-circuited magnetite/steel couple finally has a potential that equals that of steel when more steel area is exposed to the medium. A severe attack on the steel was observed when the experiment was terminated.

Figure 6:
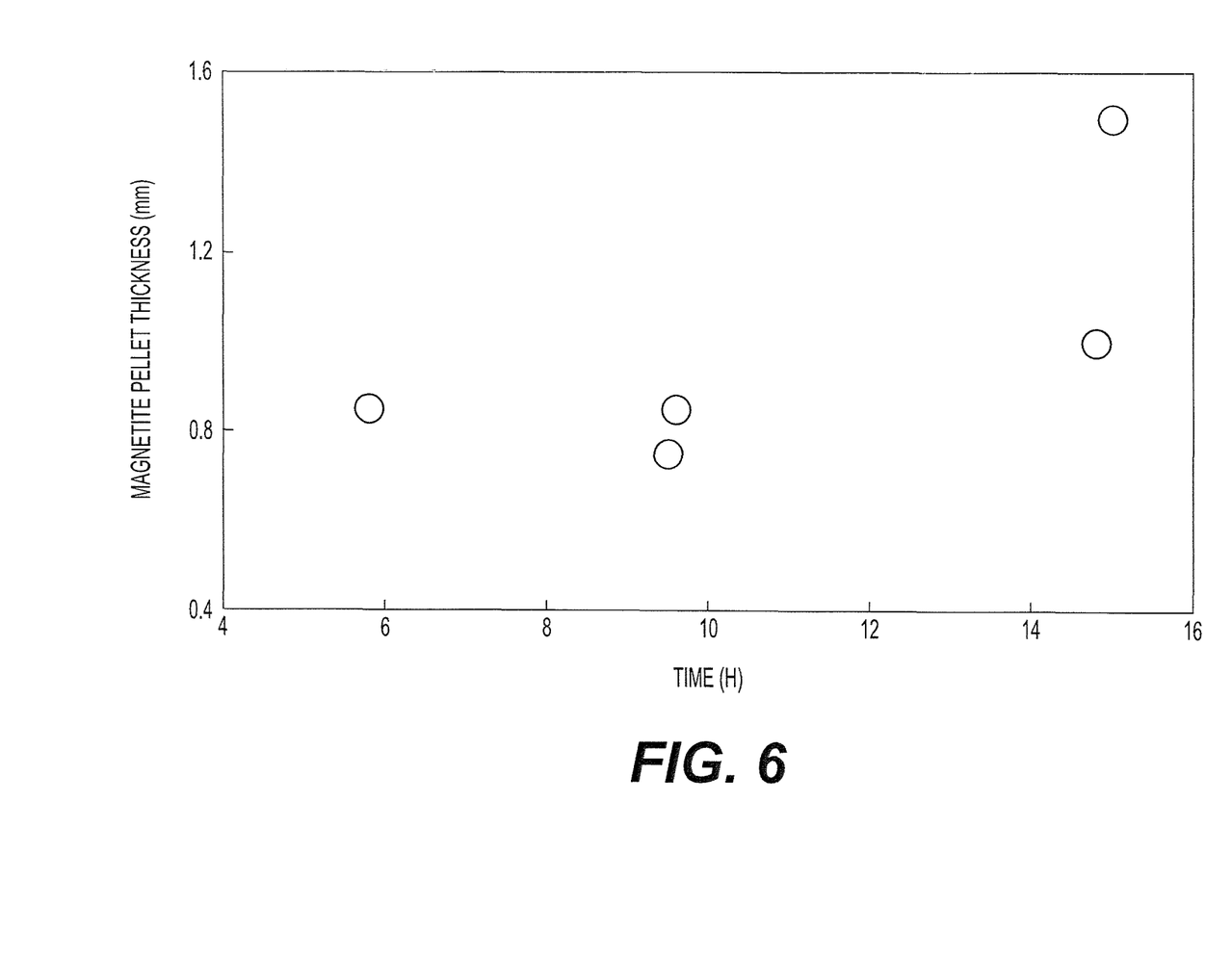
FIG. 6 is a plot showing magnetite sample thickness as a function of time for total dissolution of the magnetite in 5% HCl solution at 60° C.

The severity of the steel attack depends greatly on the magnetite/iron area ratio being more severe when the exposed area of iron was small, due to the large shift in its potential in the anodic direction when coupled galvanically to the magnetite. The variation in the time required for the potential to shift towards that of steel is different from one electrode to another when the thickness of the magnetite pellet was kept constant. This may be due to the variations in the characteristics of each magnetite pellet, since no two magnetite pellets are identical. When the magnetite thickness was increased, the time needed for the potential shift towards that of steel was also increased, as shown in FIG. 6. This indicates that a longer time is required to dissolve the thicker magnetite pellet or to penetrate it.

The above results of the potential variation with time do not show the minimum time needed for a complete removal of the oxide from the steel surface. However, it provides a clear indication of the removal process trend, and, more importantly, it shows the time when the iron comes under attack by the acid used for cleaning. In order to confirm the increased corrosion attack on the steel substrate when the galvanic potential of the magnetite/steel couple is between that of magnetite and steel, as seen in FIG. 4, a series of linear polarization resistance ($R_P$) measurements were made at different times, using an electrode made from a 0.85 mm thick magnetite pellet coupled with the iron electrode.

Figure 7:
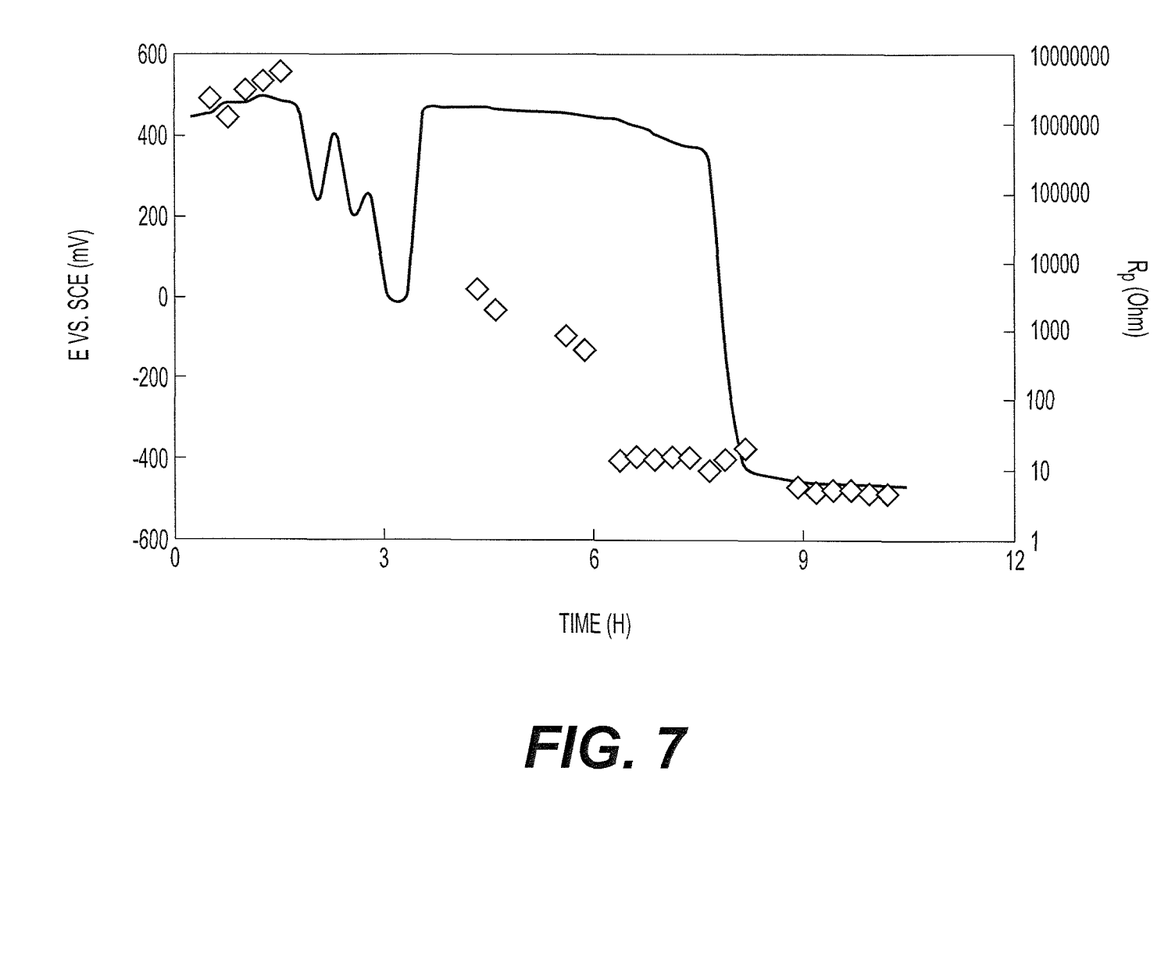
FIG. 7 is a plot showing variation of potential and linear polarization resistance for a 0.85 mm thick magnetite pellet coupled with steel vs. a standard calomel electrode (SCE) in 5% HCl solution at 60° C.

Linear polarization resistance ($R_P$) was measured using a Gill AC potentiostat manufactured by ACM Instruments of Cumbria, United Kingdom with a scan rate of 0.16 mV/s in the range of 10 mV from the corrosion potential. FIG. 7 shows that $R_P$ values were high in the early stage of the cleaning process. The high values of $R_P$ coincide with potentials that are close to that of magnetite. $R_P$ tends to decrease with time and becomes very low at a time of about 400 minutes, which indicates that the iron is corroding. This large decrease in the $R_P$ value is observed when the couple potential is near the steel potential.

It is to be understood that the steel panel with an integrated corrosion sensor is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A steel panel with an integrated corrosion sensor, comprising:
   a steel panel having an opening formed therethrough;
   a hollow insulator secured to the steel panel within the opening formed therethrough;

a steel core mounted in the hollow insulator, the steel core having opposed first and second surfaces;

a reference electrode, wherein the reference electrode comprises a saturated calomel electrode;

a voltmeter electrically connected between the reference electrode and the first surface of the steel core;

a layer of magnetite formed on the second surface of the steel core; and an alarm in electrical communication with the voltmeter, the alarm being configured for generating an alarm signal when the voltmeter detects a corrosion potential at a preset threshold potential.

2. The steel panel with an integrated corrosion sensor as recited in claim 1, wherein the steel panel has opposed first and second surfaces, the first surface of the steel panel being level with the first surface of the steel core, and the second surface of the steel panel being level with the second surface of the steel core.

3. The steel panel with an integrated corrosion sensor as recited in claim 1, wherein the hollow insulator comprises a hollow cylindrical ring.

4. The steel panel with an integrated corrosion sensor as recited in claim 1, wherein the hollow insulator comprises an epoxy resin.

5. A magnetite corrosion sensor, comprising:

a hollow insulator adapted for embedding in a steel panel;

a steel core mounted in the hollow insulator, the steel core having opposed first and second surfaces;

a reference electrode, wherein the reference electrode comprises a saturated calomel electrode;

a voltmeter electrically connected between the reference electrode and the first surface of the steel core;

a layer of magnetite formed on the second surface of the steel core; and an alarm in electrical communication with the voltmeter, the alarm being configured for generating an alarm signal when the voltmeter detects a corrosion potential at a preset threshold potential.

6. The magnetite corrosion sensor as recited in claim 5, wherein the hollow insulator comprises a hollow cylindrical ring.

7. The magnetite corrosion sensor as recited in claim 5, wherein the hollow insulator comprises an epoxy resin.

* * * * *